United States Patent
Teodorescu et al.

(10) Patent No.: US 12,201,486 B2
(45) Date of Patent: Jan. 21, 2025

(54) ULTRAPORTABLE SYSTEM FOR INTRAOPERATIVE ISOLATIVE AND REGULATION OF SURGICAL SITE ENVIRONMENTS

(71) Applicant: SurgiBox Inc., Brookline, MA (US)

(72) Inventors: Debbie Lin Teodorescu, Brookline, MA (US); Daniel D. Frey, Natick, MA (US); Sally A. Miller, Cambridge, MA (US); Robert J. Smalley, Boston, MA (US)

(73) Assignee: SurgiBox Inc., Cambridge, MA (US)

( * ) Notice: Subject to any disclaimer, the term of this patent is extended or adjusted under 35 U.S.C. 154(b) by 1157 days.

(21) Appl. No.: 16/317,892

(22) PCT Filed: Jul. 14, 2017

(86) PCT No.: PCT/US2017/042266
§ 371 (c)(1),
(2) Date: Jan. 15, 2019

(87) PCT Pub. No.: WO2018/014003
PCT Pub. Date: Jan. 18, 2018

(65) Prior Publication Data
US 2021/0290337 A1    Sep. 23, 2021

Related U.S. Application Data

(60) Provisional application No. 62/362,893, filed on Jul. 15, 2016.

(51) Int. Cl.
*A61B 90/00* (2016.01)
*A61B 46/27* (2016.01)
(Continued)

(52) U.S. Cl.
CPC .............. *A61B 90/40* (2016.02); *A61B 46/27* (2016.02); *A61B 2017/00557* (2013.01); *A61B 2090/0807* (2016.02); *A61B 2090/401* (2016.02)

(58) Field of Classification Search
CPC .... A61G 10/02; A61G 10/023; A61G 10/005; A61G 10/04; A61G 13/108; A61B 90/40;
(Continued)

(56) References Cited

U.S. PATENT DOCUMENTS

| 3,051,164 A | 8/1959 | Trexler |
| 3,692,024 A | 9/1972 | Von |

(Continued)

FOREIGN PATENT DOCUMENTS

| CN | 204274654 U | 4/2015 |
| CN | 204394702 U | 6/2015 |

(Continued)

OTHER PUBLICATIONS

Authorized officer Lee W.Young, International Search Report/Written Opinion in PCT/US2017/042266 mailed Sep. 28, 2017, 9 pages.

(Continued)

*Primary Examiner* — Adam Baker
(74) *Attorney, Agent, or Firm* — Fish & Richardson P.C.

(57) ABSTRACT

A portable surgical system including a transparent and flexible plastic enclosure (1) is disclosed. The enclosure is attached reversibly to the patient's body encompassing the surgical site such as to isolate and regulate the immediate environment of the surgical site, and to reduce bodily fluid splatters from the surgical site to the surgical providers. The enclosure is inflated with filtered air. Arm ports (8) are integrated into the enclosure to allow access to the inside of the enclosure by either provider arms or augmenting instru-
(Continued)

mentation taking the place of arms such as laparoscopes or robots. Material ports (10) maintain enclosure environmental integrity but allow the passing of anatomical specimens, instruments, and other materials into and out of the enclosure (1) during a procedure. The portable surgical system is lightweight and can be used in conventional operating rooms to improve sterility, or in other circumstances where no operating room is available, such as field hospitals.

17 Claims, 14 Drawing Sheets

(51) Int. Cl.
*A61B 90/40* (2016.01)
*A61B 17/00* (2006.01)

(58) Field of Classification Search
CPC ... A61B 2090/401; A61B 46/27; A61B 46/10; A61B 46/20; A61B 46/23
USPC .......................................................... 128/849
See application file for complete search history.

(56) References Cited

U.S. PATENT DOCUMENTS

| | | | |
|---|---|---|---|
| 3,850,172 A * | 11/1974 | Cazalis ................. | A61B 90/40 600/21 |
| 4,275,719 A * | 6/1981 | Mayer .................... | A61B 90/40 128/849 |
| 4,367,728 A | 1/1983 | Mutke | |
| 4,865,049 A | 9/1989 | Gatti | |
| 4,950,222 A * | 8/1990 | Scott .................... | A61G 13/108 312/1 |
| 5,083,558 A | 1/1992 | Thomas et al. | |
| 5,170,804 A * | 12/1992 | Glassman .............. | A61B 50/10 128/849 |
| 5,299,582 A | 4/1994 | Potts | |
| 5,728,041 A | 3/1998 | Fowler, Jr. | |
| 5,979,450 A * | 11/1999 | Baker .................... | A61B 46/10 128/850 |
| 6,001,057 A * | 12/1999 | Bongiovanni ......... | A62B 31/00 5/629 |
| 6,199,551 B1 | 3/2001 | Kuslich | |
| 2002/0045796 A1 | 4/2002 | O'Connor | |
| 2003/0060831 A1 | 3/2003 | Bonutti | |
| 2007/0102005 A1 | 5/2007 | Bonutti | |
| 2008/0041399 A1 | 2/2008 | Kriek | |
| 2008/0047567 A1 | 2/2008 | Bonutti | |
| 2009/0124987 A1* | 5/2009 | Eriksson ........... | A61F 13/00068 604/304 |
| 2009/0216069 A1 | 8/2009 | Woodcock et al. | |
| 2010/0234794 A1 | 9/2010 | Weadock et al. | |
| 2011/0301459 A1 | 12/2011 | Gharib | |
| 2016/0008081 A1 | 1/2016 | Forsell | |
| 2016/0074268 A1 | 3/2016 | Breegi | |
| 2016/0166455 A1 | 6/2016 | Steinert | |
| 2016/0331461 A1 | 11/2016 | Cheatham, III | |
| 2017/0340407 A1 | 11/2017 | Ahrens | |
| 2018/0085559 A1 | 3/2018 | Laby et al. | |
| 2024/0156566 A1 | 5/2024 | Teodorescu | |

FOREIGN PATENT DOCUMENTS

| | | |
|---|---|---|
| CN | 204394708 U | 6/2015 |
| GB | 1604033 | 12/1981 |
| JP | H0670725 U | 10/1994 |
| WO | WO 1986/06272 | 4/1985 |
| WO | WO/9107921 | 6/1991 |
| WO | WO1993016741 | 9/1993 |
| WO | WO 2005/092229 | 3/2004 |
| WO | WO2011041665 A1 | 4/2011 |
| WO | WO 2013/012367 | 1/2013 |
| WO | WO 2014/145032 | 3/2013 |
| WO | WO 2014/189874 | 11/2014 |
| WO | WO 2016/102018 | 6/2016 |
| WO | WO 2020/061037 | 3/2020 |
| WO | WO 2020/227706 | 11/2020 |
| WO | WO 2022/182394 | 9/2022 |

OTHER PUBLICATIONS

TH Office Action in Thai Appln. No. 1901000182, dated Nov. 16, 2020, 4 pages (with English translation).
EP Communication in European Appln. No. 17828590.4, dated May 12, 2020, 7 pages.
CN Office Action in Chinese Appln. No. 201780055697.4, dated May 8, 2021, 16 pages.
EP Extended European Search Report in European Appln. No. 1782590.4, dated Jun. 28, 2019, 9 pages.
PCT International Preliminary Report on Patentability in International Appln. No. PCT/US2017/042266, dated Jan. 15, 2019, 9 pages.
AU Office Action in Australian Application No. 2017297605, dated Dec. 24, 2021, 3 pages.
IL Office Action in Israeli Appln. No. 264163, dated Dec. 27, 2021, 12 pages (with English translation).
KR Office Action in Korean Appln. No. 7004609, dated Jan. 19, 2022, 10 pages (with English translation).
Allegranzi et al., "Burden of endemic health-care-associated infection in developing countries: systematic review and meta-analysis," The Lancet, Jan. 15, 2011, 377(9761):228-41.
American Society of Heating, Refrigerating and Air-Conditioning Engineers, "2011 ASHRAE Handbook—HVAC Applications: Heating Ventilation and Air Conditioning Applications," Jun. 15, 2011, 1104 pages.
Edmiston et al., "Molecular epidemiology of microbial contamination in the operating room environment: Is there a risk for infection?," Surgery, Oct. 1, 2005, 138(4):573-82.
Kilinc, "A review of isolation gowns in healthcare: fabric and gown properties," Journal of Engineered Fibers and Fabrics, Sep. 2015, 10(3), 11 pages.
Sehulster et al., "Guidelines for Environmental Infection Control in Health-Care," May 27, 2003, retrieved Nov. 1, 2021 from URL: <https://www.cdc.gov/mmwr/preview/mmwrhtml/rr5210a1.htm>, 60 pages.
Teodorescu et al., "An Ultraportable Device Platform for Aseptic Surgery in Field Settings," Journal of Medical Devices, Jun. 1, 2016, 10(2), 2 pages.
Teodorescu et al., "SurgiBox: An ultraportable system to improve surgical safety for patients and providers in austere settings," 2017 IEEE Global Humanitarian Technology Conference (GHTC), Oct. 19, 2017, 5 pages.
Whyte et al., "The importance of airborne bacterial contamination of wounds," Journal of Hospital Infection, Jun. 1, 1982, 3(2):123-35.
AU Office Action in Australian Appln. No. 2017297605, dated May 20, 2022, 4 pages.
EP Extended Search Report in European Appln. No. 21216566.6, dated May 16, 2022, 9 pages.
CA Office Action in Canadian Appln. No. 3,030,844, dated Apr. 13, 2022, 4 pages.
IL Office Action in Israeli Appln. No. 2627195, dated Jul. 27, 2022, 10 pages (with English translation).
ashrae.org, "Ventilation of Health Care Facilities 170-2013," Feb. 2014, retrieved Sep. 28, 2022 from URL <https://permissions.iengineering.com/Content/pdf>, 28 pages.
EP Notice of Opposition in European Appln. No. 17828590.4, dated Sep. 28, 2022, 30 pages.
Kunze, "Mobiler Laminar Flow—eine neue Technologie fur den OP-Saal," Medizintechnik, Jan. 2008, 128(6):213, 36 pages (with English translation).
Spagnolo et al., "Operating theatre quality and prevention of surgical site infections," Journal of Preventive Medicine and Hygiene, Sep. 2013, 54(3):131, 7 pages.

(56) References Cited

OTHER PUBLICATIONS

AU Office Action in Australian Appln. No. 2017297605, dated Oct. 13, 2022, 6 pages.
CN Office Action in Chinese Appln. No. 202210145091.2, mailed on Mar. 27, 2024, 19 pages (with English translation).
PCT International Preliminary Report on Patentability in International Appln. No. PCT/US2022/020041, mailed on Sep. 12, 2023, 14 pages.
PCT International Search Report and Written Opinion in International Appln. No. PCT/US2022/020041, mailed on Mar. 11, 2022, 22 pages.

* cited by examiner

ULTRAPORTABLE SYSTEM FOR INTRAOPERATIVE ISOLATIVE AND REGULATION OF SURGICAL SITE ENVIRONMENTS

CROSS REFERENCE TO RELATED APPLICATION

This application is a U.S. National Stage Application under 35 USC § 371 and claims the benefit of International Patent Application No. PCT/US2017/042266 filed on Jul. 14, 2017, entitled "Ultraportable System for Intraoperative Isolative and Regulation of Surgical Site Environments." which claims priority from and the benefit of U.S. Provisional Patent Application No. 62/362,893 filed on Jul. 15, 2016 and titled "Modular Surgical Suite", both of which are hereby incorporated by reference for all purposes as if fully set forth herein.

BACKGROUND OF THE INVENTION

I. Field of the Invention

Exemplary embodiments of the present invention relate to a portable surgical system for regulating intra-operative environments over surgical sites; and to methods for implementing and using the same.

II. Discussion of the Background

Over 25% of the global disease burden requires surgical therapy, which could prevent over 18 million deaths per year. These range from obstetric complications to traumas to infections to cancer and beyond. Yet 2 billion people have no meaningful access to safe surgical care, and 2-3 billion more have access only to unsterile surgeries in contaminated environments, leading to disproportionate rates of surgical infections. Innovations in this field typically focus upon making operating rooms and operating room ventilation systems more mobile, such as in tent format. However, such systems remain costly to purchase and to maintain. Moreover, such systems are difficult to transport rapidly to remote areas. At the same time, over 85,000 medical providers are infected by patient bodily fluids annually, with 90% of infected providers worldwide having been exposed while working in low-resource settings. While personal protective equipment mitigates these risks to some extent, there is a definite trade-off between the level of protection and both the cost as well as the user comfort, which is well-documented to correspond to user compliance.

Exemplary embodiments of the present invention aim to address both challenges of patient and provider intraoperative exposure to infectious risks by implementing an ultraportable, self-contained, passive and active, bilateral barrier against exchange of contaminants between incisions and the greater surgical area.

The above information disclosed in this Background section is only for enhancement of understanding of the background of the invention and therefore it may contain information that does not form any part of the prior art.

SUMMARY OF THE INVENTION

Exemplary embodiments of the present invention provide a portable surgical system for regulating intra-operative environments over surgical sites.

The surgical system includes a transparent, soft plastic enclosure which is attached reversibly around the patient's body immediately encompassing the planned surgical site. The enclosure integrates arm ports to allow access to the inside of the enclosure by either provider arms or augmenting instrumentation taking the place of arms such as laparoscopes or robots. Material ports which can be repeatedly opened and closed are used to maintain enclosure environmental integrity but allow the passing of anatomical specimens, instruments, and other materials into and out of the enclosure during a procedure. Such an enclosure may incorporate into the sterile field particular to a given procedure, one or more sections to hold instrument trays. The enclosure may be filled with air from the environmental control system through an inlet, valve, and manifold system integrated into the enclosure. The environmental control system is capable of enacting such pre-selected controls required for a given procedure such as HEPA filtration, humidity modulation, heating or cooling, or change of gas composition. The surgical system is lightweight and may be used in conventional operating rooms to improve sterility, or in other circumstances where no operating room is available, such as field hospitals.

Additional features of the invention will be set forth in the description which follows, and in part will be apparent from the description, or may be learned by practice of the invention.

An exemplary embodiment of the present invention discloses a portable surgical system for regulating intra-operative environments over surgical sites. The surgical system may include a disposable component including the enclosure with patient interface, and a reusable component including an environmental control system and optional external support frame.

The disposable component may include an operating section and an instrument section separated from the operating section. The environmental control component is connected with the enclosure such as to control the environment inside the enclosure. An external support frame may be configured to connect with the disposable component to provide mechanical support to the disposable component.

An exemplary embodiment of the present invention also discloses a method for using a portable surgical system including the following steps: laying a patient on top of the operating table; placing instrument tray holder over patient legs; performing skin disinfecting procedure; placing the disposable component over surgical site with the operating-section cranial and instrument-section portion caudal; placing one pair of surgical gloves in the enclosure for each planned user, at the arm ports corresponding to the user's expected position; placing an instrument tray via material port in the instrument-section; engaging environmental control system; attaching an external frame to the instrument tray holder; pulling tethers from the external top of enclosure and securing to frame in top clip; placing arms inside enclosure and applying gloves.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
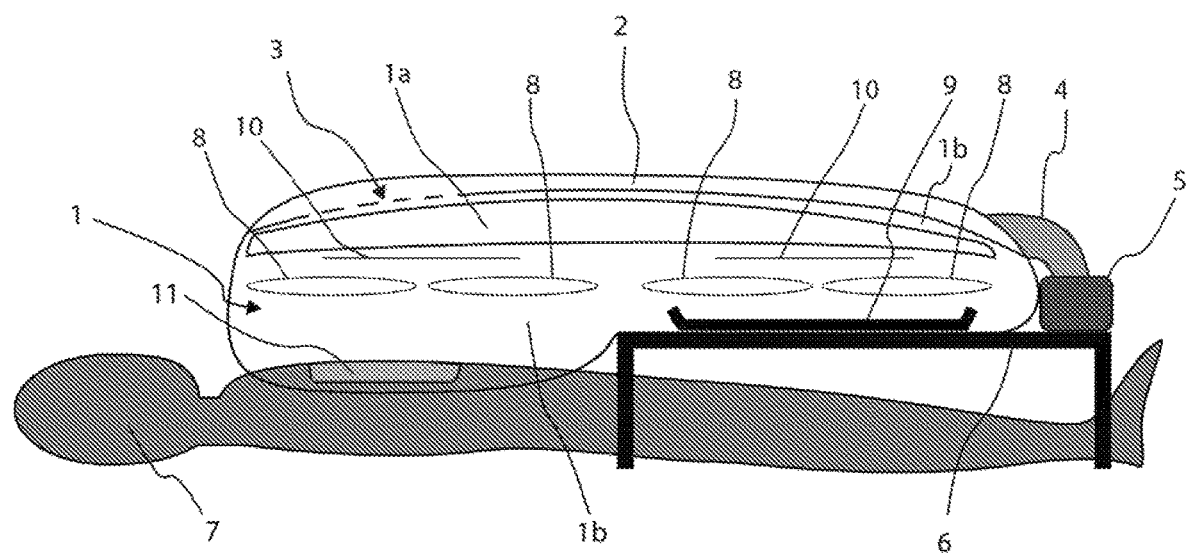
FIG. 1 is a side view of an inflated portable surgical enclosure adhered to the patient's torso surgical site via incise drape, with air inflow from air supply in enclosure side closest to patient feet, directed in cranial longitudinal direction over the patient's surgical site.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

It will be understood that when an element or layer is referred to as being "on" or "connected to" another element or layer, it can be directly on or directly connected to the other element or layer, or intervening elements or layers may be present. In contrast, when an element or layer is referred to as being "directly on" or "directly connected to" another element or layer, there are no intervening elements or layers present. It will be understood that for the purposes of this disclosure, "at least one of X, Y, and Z" can be construed as X only, Y only, Z only, or any combination of two or more items X, Y, and Z (e.g., XYZ, XY, YY, YZ, ZZ).

FIG. 1 illustrates a preferred embodiment of a portable surgical system. The portable surgical system includes a flexible plastic enclosure 1 configured to be supplied with air under positive pressure via an environmental control system 5. The enclosure 1 may be adhered to a surgical site of a patient 7 via an incise drape 11 as shown in FIG. 1. The incise drape may be a flexible plastic drape and may include a removable skin adhesive on one side, with or without antimicrobial impregnation. The portable surgical system may be configured such that filtered air is blown or passed through a longitudinal tubular valve with walls of flexible, collapsible plastic such as polyethylene 2 and through a manifold with perforations 3. The filtered air may be blown such as to cause an essentially uniform laminar air flow onto the surgical site and through the enclosure.

Figure 2:
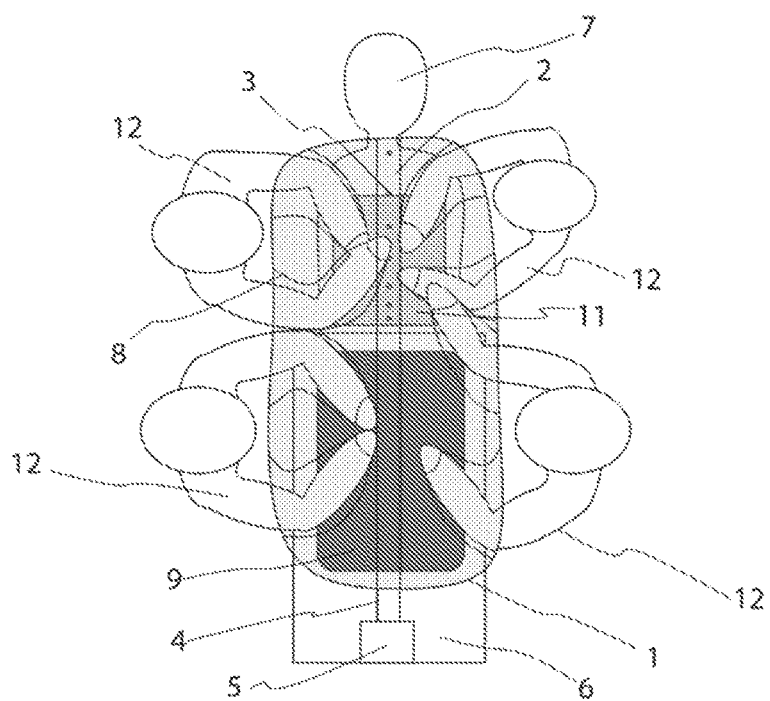
FIG. 2 is a top view of the inflated portable surgical enclosure from FIG. 1 with two users working via arm ports in operating-section on the torso surgical site, and two users working via arm ports in instrument-section.

The portable surgical system may include a plurality of ports, such as arm ports 8 and material ports 10 shown in FIGS. 1 and 2. In an exemplary embodiment the portable surgical system may include four pairs of integrated, cuffed sleeves in the arm ports 8. The ports 8 provide users with access to the inside of the enclosure, as shown in FIG. 2. The material ports 10 may be used to move the surgical tray 9 to the inside of the enclosure 1 prior to the surgical procedure. The portable surgical system may further include an instrument tray holder 6 which may be placed around the legs of the patient 7. The tray 9 may be disposed on top of the instrument tray holder 6.

In the preferred embodiment shown in FIG. 1, the perforations which define the manifold outlets 3 in the overhead tube decrease in density along the remainder of the manifold over the operating-section such that the airflow over the incise drape 11 is essentially constant. If the environmental control system 5 is shut off, the flexible overhead tube 2 is pinched shut, thus sealing the enclosure 1 and preventing backflow into the fan and filter 5.

The portable surgical system may include a surgical enclosure, a frame, and an environmental control system.

A. Structure of Surgical Enclosure

In an exemplary embodiment the surgical enclosure may be disposable, such as the enclosure 1 shown in FIG. 1. In an exemplary embodiment the surgical enclosure may be supplied folded like a surgical gown. When set up, the surgical enclosure may comprise one or more top view panels of optically-clear plastic 1a, such as polyvinyl chloride. The remainder of the surgical enclosure sides may comprise a flexible, impermeable plastic, such as low-density polyethylene. The sides of the instrument-section may be shorter than those of the operating-section, in order to fit over an instrument tray holder. In the preferred embodiment shown in FIG. 1, the bottom of the enclosure is continuous with the sides.

The panel of incise drape 11 may be incorporated into the bottom of the operating-section as shown in FIG. 1. The incise drape serves as the interface with the patient body. The size and shape of the incise drape 11 may be configured to cover the surgical site on the patient's body while essentially excluding body surface outside the surgical site. Consequently, as seen in FIG. 1, only the surgical site of the patient's body (i.e. area covered by the incise drape 11) is included within the surgical enclosure, while the remainder of the patient body is excluded from the sterile field. By excluding from the surgical enclosure the unnecessary body surface, the efficacy of the system is significantly improved since the patient's body surface contributes to environment contamination inside the enclosure. In particular, the exclusion of high-contaminant regions such as the oropharynx or the genitals is likely to significantly improve the efficacy of the system. The surgical enclosure 1 may include incise drapes 11 of different shapes and sizes and may be disposed at different positions on the surgical enclosure such as to fit the needs of different types of medical procedures. The bottom corners of the surgical enclosure may include straps for securing the enclosure to the patient or to the operating table for additional stability.

Figure 9:
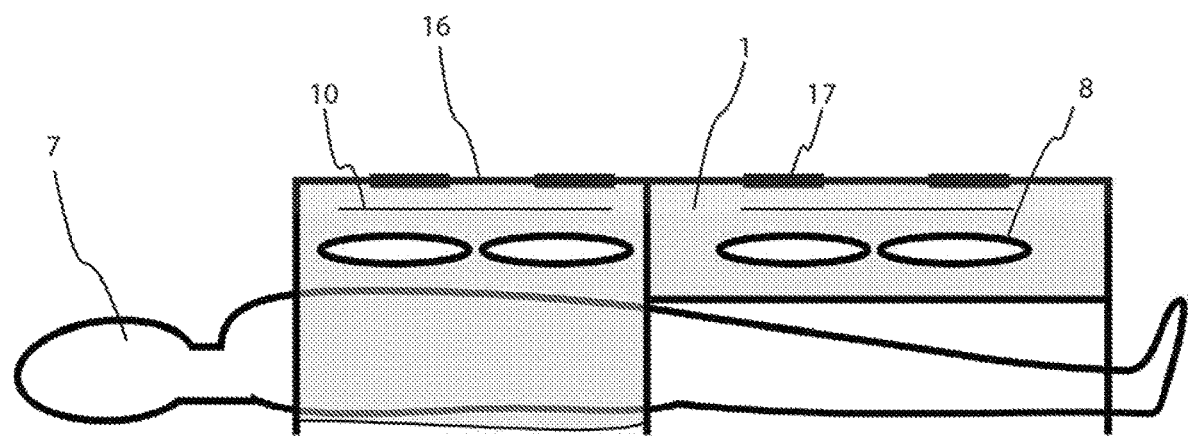
FIG. 9 is a side view of an alternate embodiment of the surgical enclosure and frame, in which the rigid frame fully supports the enclosure with frame attachment to each of the sides defining the top of the enclosure. The enclosure extends circumferentially around the patient torso.
Figure 10:
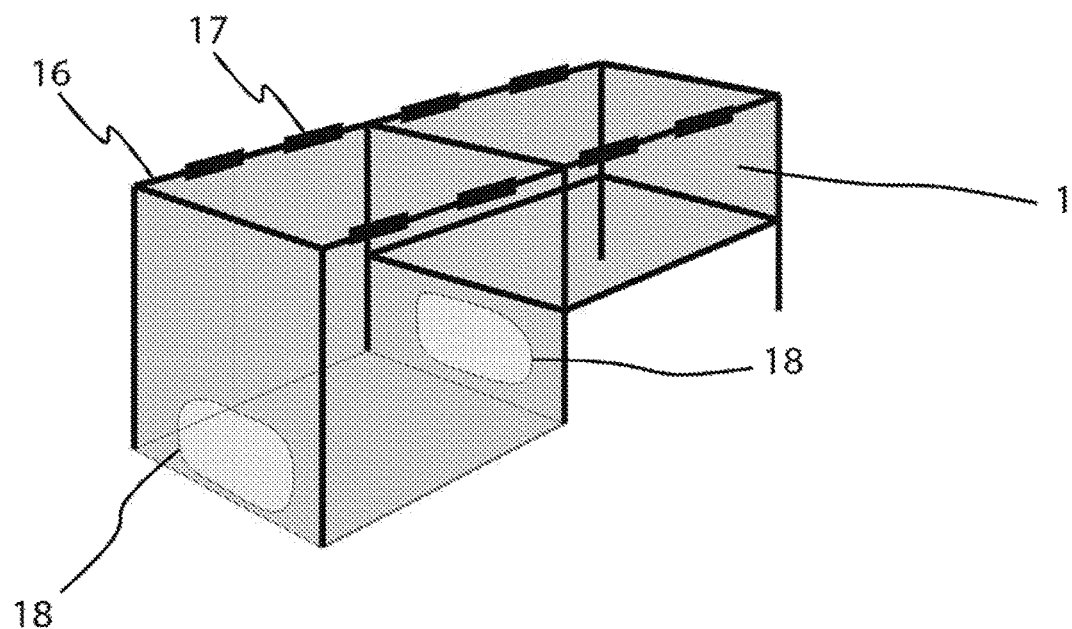
FIG. 10 shows an oblique perspective view of the frame and plastic enclosure shown in FIG. 9.

FIGS. 9 and 10 illustrate a side view and a perspective view, respectively, of a second preferred embodiment of the portable surgical system. In the second preferred embodiment the portable surgical system includes an incise drape-less surgical enclosure 1 wherein the operating-section of the patient is placed inside the enclosure and wherein the bottom of the enclosure remains continuous with the sides at the level of the instrument-section. In the operating-section of the enclosure, one side of the enclosure may be elongated so as to enable tucking under the patient body, thereby eliminating the continuous bottom panel. After passing under the patient body, the residual length of the elongated side may be secured to the contralateral enclosure side along the free edge of the elongated side. The cranial end of the operating-section 18 as well as the interface with the instrument-section 18 may be secured against the patient via integrated straps.

Embodiments of the invention are described herein with reference to figures and illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

The portable surgical systems disclosed herein may include alternate or additional sections which could be added based on procedural needs, such as to accommodate additional instrument trays or users. The above embodiments presented in this disclosure merely serve as exemplary embodiments and it will be apparent to those skilled in the art that various modifications and variations can be made in the present invention without departing from the spirit or scope of the invention.

B. Structure of Frame

Figure 3:
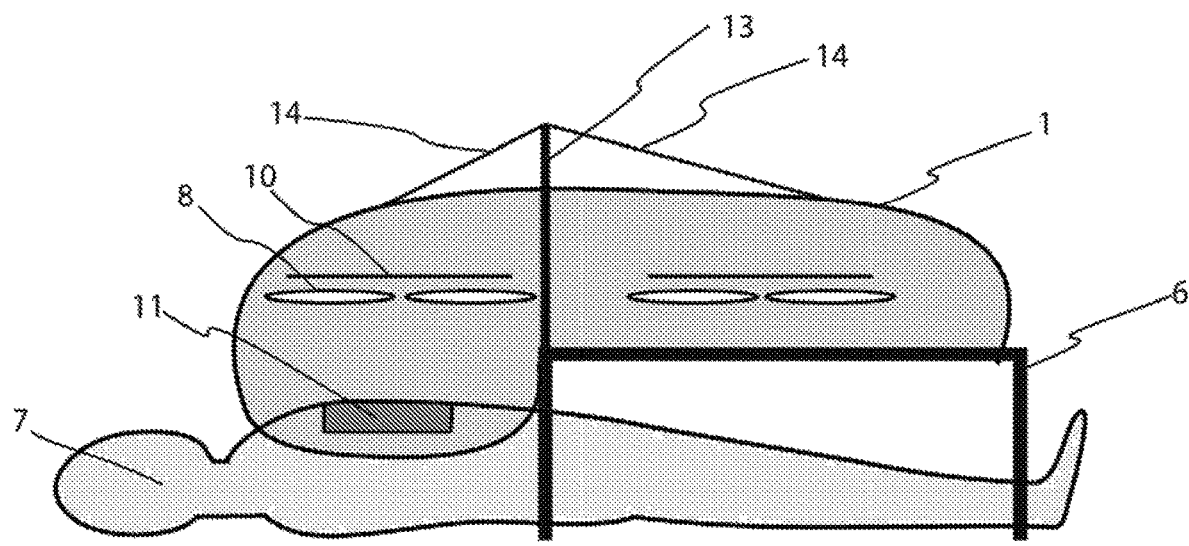
FIG. 3 is a side view of an alternate embodiment of the surgical enclosure which utilizes a central frame and oblique tethers in cranial and caudal directions to assist with holding up the enclosure.
Figure 4:
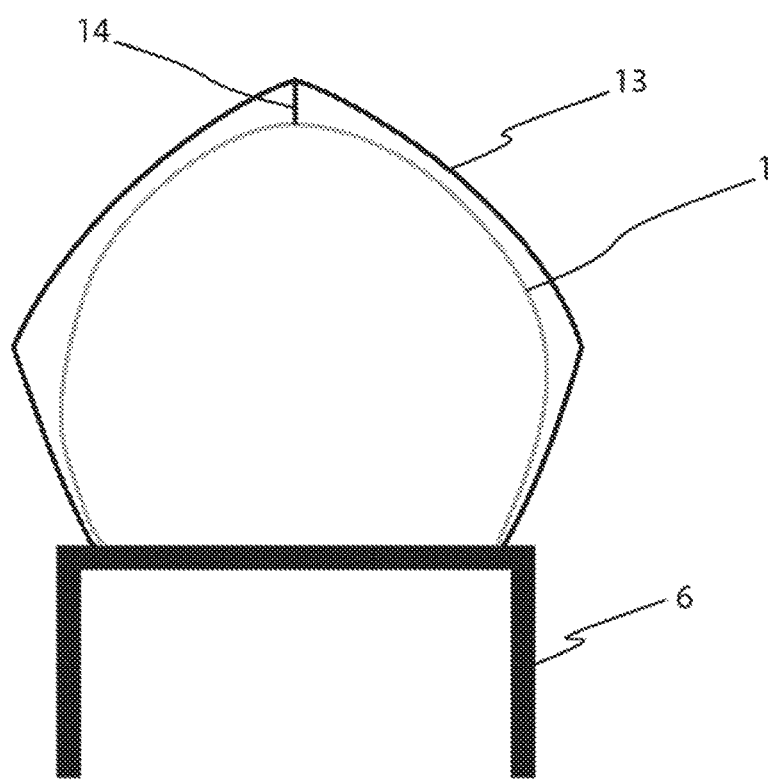
FIG. 4 is an axial view perpendicular to the view illustrated in FIG. 3 showing the shape of the central frame and the tethers to support it. Patient, instrument tray, and ports are excluded from illustration.

In an exemplary embodiment, illustrated in FIGS. 3 and 4, the portable surgical system may include a central frame 13 and tethers 14 intended to support the enclosure 1 in the case of a sudden pressure loss. The central frame 13 may be lightweight and/or collapsible so as to be easily transported. The frame may be made of a rigid material, such as plastic, rigid polyvinyl tubes, aluminum tubing, and other materials familiar to practitioners knowledgeable in the field. The frame may include four oblique tubes which are reversibly secured to the instrument tray holder or operating table such that the instrument tray holder or operating table form the bottom of a pentagon when viewed axially as in FIG. 4. One or more of these pieces may be connected to one another via custom connectors or hinges, configured to maintain the pentagon within the same plane. The topmost vertex of the frame may be reversibly attached to the disposable component top, such as via a formed plastic slot in the disposable component or via tether 14 only. Tethers 14 may support the plastic enclosure 1 directly underneath the frame 13, as shown in FIG. 4, as well as longitudinally over the incise drape 11 and instrument tray holder 6. Frame 13 and tethers 14 are configured to provide support to the enclosure 1 in the event of a sudden pressure loss. Various other tether arrangements may be utilized to optimize support from the central frame, depending on system requirements.

Figure 5:
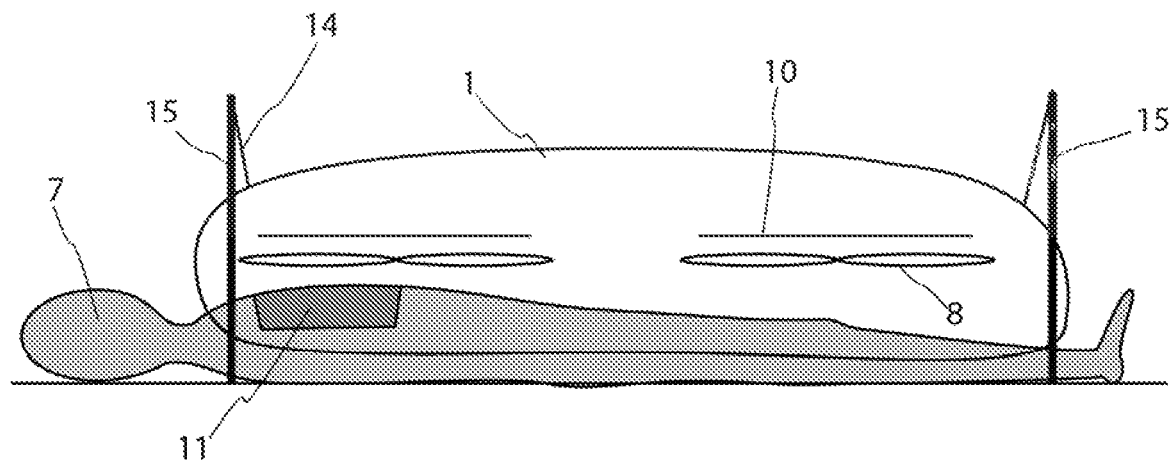
FIG. 5 is a side view of an additional alternative embodiment which utilizes two vertical frames at each of the cranial and caudal ends of the enclosure, and tethers to support the surgical enclosure.
Figure 6:
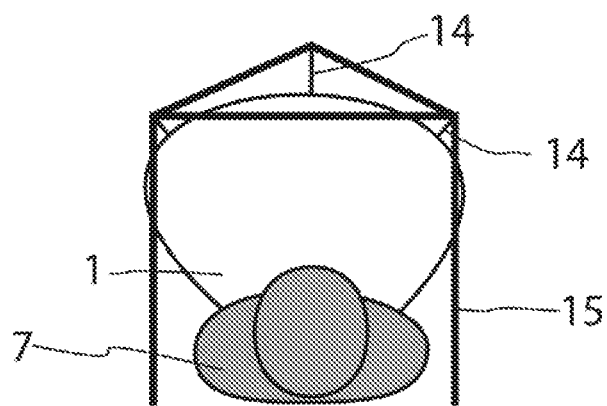
FIG. 6 is an axial view perpendicular to the view illustrated in FIG. 5 showing the shape of one of the two identical frames and the tethers which support the enclosure.
Figure 7:
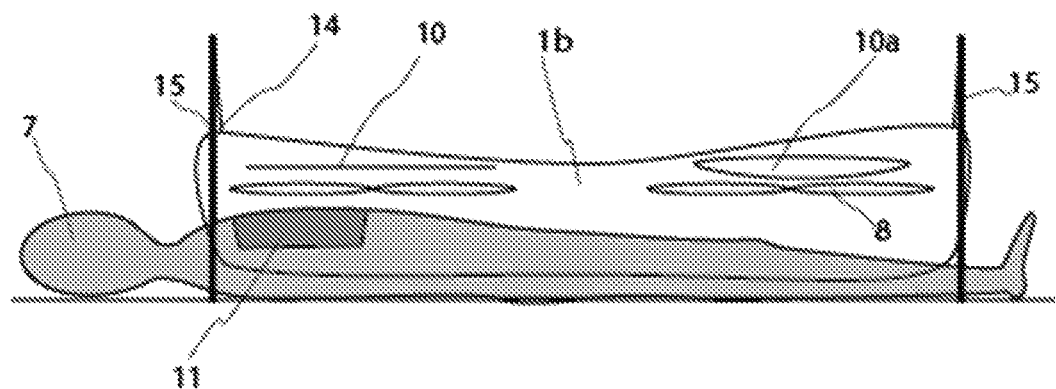
FIG. 7 is a side view of the embodiment shown in FIG. 5 and FIG. 6 demonstrating how the frame and tethers prevent the enclosure from collapsing on the surgical site in the case of sudden pressure loss.
Figure 8:
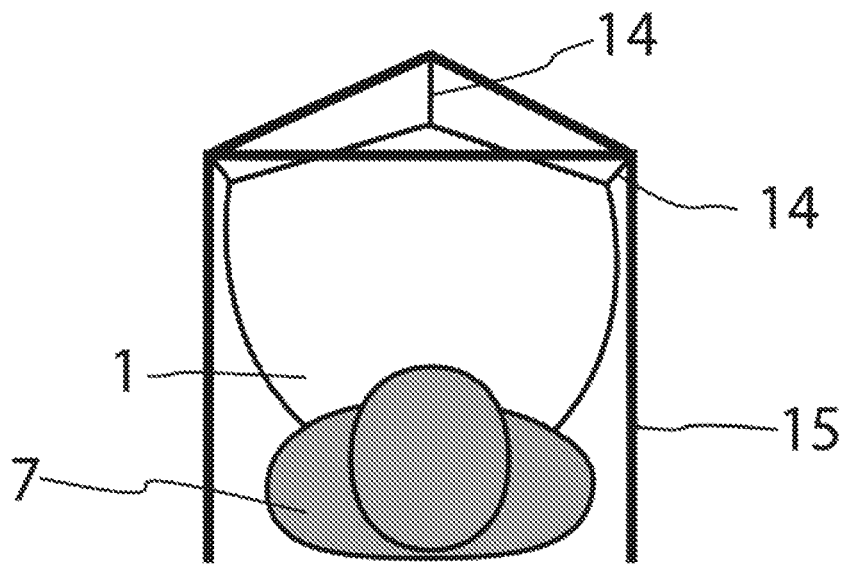
FIG. 8 is an axial view perpendicular to the view illustrated in FIG. 7.

In another exemplary embodiment the portable surgical system may include a frame 15 and tethers 14 as illustrated in FIGS. 5-8. Frame 15 and tethers 14 are configured such as to provide support to the enclosure 1 in the event of a sudden pressure loss. Instead of supporting the surgical enclosure centrally, frame 15 includes two vertical sections disposed at the cranial and caudal ends of the enclosure. FIG. 5 provides a side view of the frame 15 and tethers 14, and FIG. 6 provides a front view of the same system. FIGS. 7 and 8 show how the frame 15 and tethers 14 support the deflated enclosure 1b in the case of a sudden pressure loss, resulting from, for instance, an open port 10a.

In an exemplary embodiment the portable surgical system may include a collapsible, rigid frame 16 and a flexible plastic enclosure 1 as illustrated in FIGS. 9 and 10 and as described in the section "Structure of Surgical Enclosure"

paragraph 3 in which the surgical enclosure 1 encloses the patient's 7 torso. The portable surgical system according to this embodiment does not require a separate instrument tray holder. The enclosure 1 is reversibly sealed at the patient's suprapubic region and axillae via adjustable opening 18. This embodiment does not structurally rely on positive pressure to the extent that the previous embodiments, illustrated in FIGS. 1-8, do. The frame may comprise six vertical pieces forming the edges of two connected partial cuboids, reversibly attached to under the patient or to the operating table. As seen in FIGS. 9 and 10, the frame may include two pieces at the cranial end, two at the caudal end, and two at the junction between the operating and instrument sections. These pieces may incorporate telescoping function to accommodate different patient body sagittal abdominal diameters. These vertical pieces may be connected as shown in FIG. 9, with three pieces horizontally at the top and two additional horizontal pieces defining the instrument tray section; these latter two pieces are at a level above the patient where desired for an instrument tray holder. The frame may further include two longitudinal pieces, perpendicular to both of the above types, forming the operating section; and two additional longitudinal pieces forming the instrument section. One or more of all of these pieces may be connected via hinges or custom connectors. The enclosure may be connected to the frame reversibly 17 in such manner as to place uniform outward tension on the top view panel.

C. Ports

The various embodiments of the portable surgical system may have surgical enclosures which include a plurality of ports. The enclosure may include two major types of ports. The first type of port on the enclosure is arm ports 8, as shown in FIGS. 1, 2, 3, 5, 7, and 9, which allow access to the inside of the enclosure by either provider arms or augmenting instrumentation taking the place of arms such as laparoscopes or robots.

Figure 19:
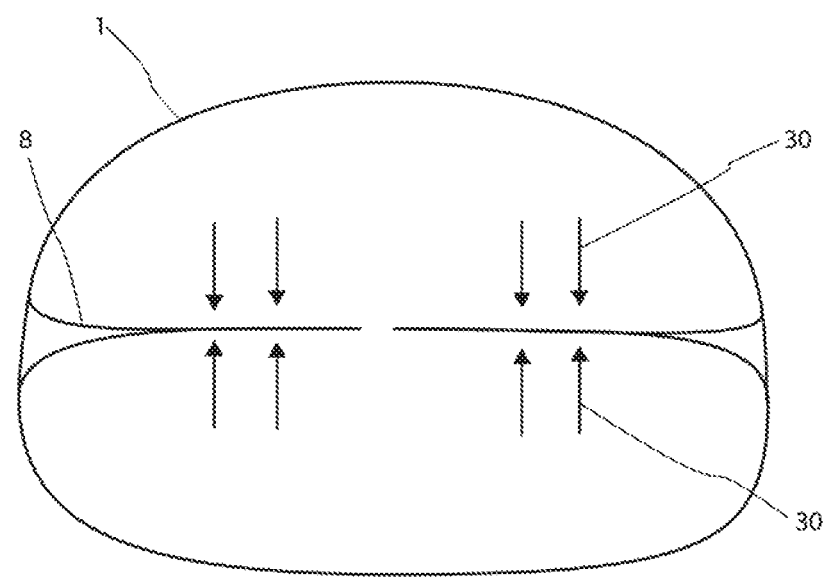
FIG. 19 is a side view at the level of the arm port, showing user sleeves and gloves in an inflated enclosure are pinched together by the positive pressure in the surgical enclosure prior to their use.

The number of arm ports is dependent on procedural need. The preferred embodiments illustrated in FIGS. 1, 2, 3, 5, 7, and 9 include four pairs of arm ports 8, two on each side of the enclosure 1. Depending on use scenario, the arm ports may take three major forms. The first form for the arm port is a simple opening in the side of the enclosure which seals reversibly against user arms. The second form for the arm port is a sleeve as shown by 8 in FIG. 2, which is a hollow cylinder or frustrated cone of impermeable plastic that tapers toward the inside of the enclosure away from the wall. The length of the sleeve is adequate to permit ergonomic handoff of instruments among ports at contralateral ends of the system. The material of the sleeve may be the same as the one used for the enclosure side, or it can be a different one, such as a material used in surgical gown sleeves. The sleeve end may be free or may incorporate a cuff of elastic material to fit against the user wrist. The third form for the arm port is the same as the second form, but ending in a glove. FIG. 19 shows a side view at the level of the arm port, showing user sleeves and gloves in an inflated enclosure. The user sleeves and gloves are pinched together by the positive pressure in the surgical enclosure prior to their use.

The second type of port on the enclosure is a materials port 10, as shown in FIGS. 1, 3, 5, 7 and 9, which allows the instrument tray 9 and instruments to be moved into the enclosure 1 prior to the procedure. Additionally, the port allows materials to be moved in and out of the enclosure throughout the surgical procedure. In the case of a caesarean section, it is imperative that the newborn child can be quickly and ergonomically passed out of the enclosure so it can receive care.

Figure 15:
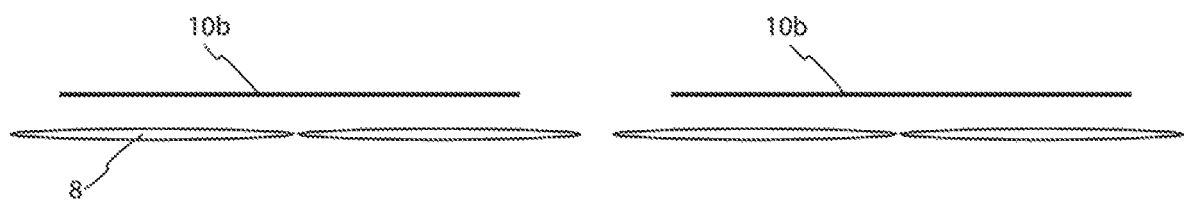
FIG. 15 shows an exemplary embodiment of the material ports.
Figure 16:
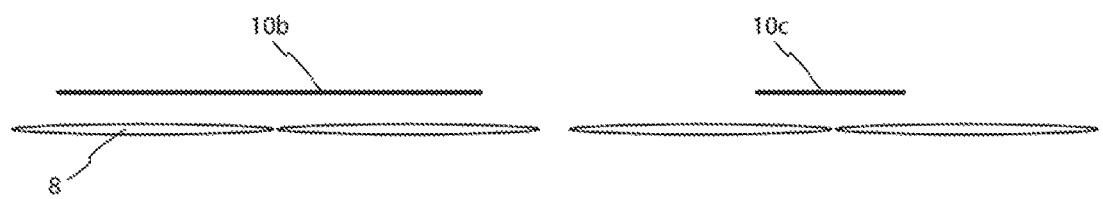
FIG. 16 shows an alternate embodiment of the material ports with different port sizes.
Figure 17:
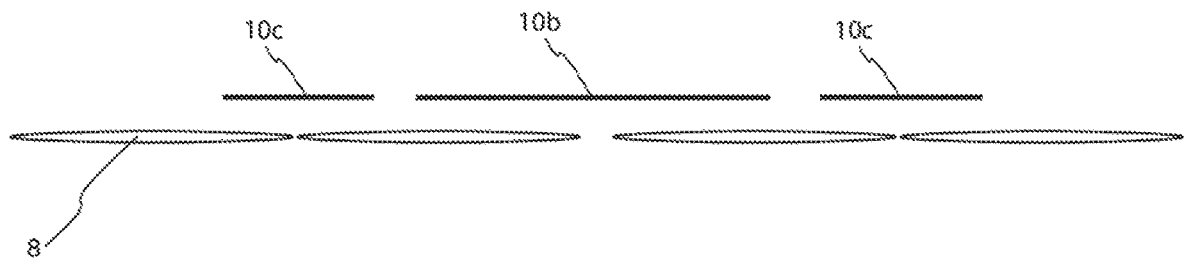
FIG. 17 shows an alternate embodiment of the material ports, in which there is a small port above each set of sleeves and a larger port in the middle.
Figure 18:
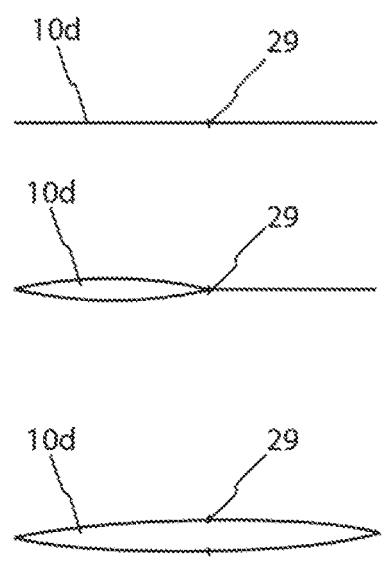
FIG. 18 shows an alternate embodiment of the material port, in which a bimodal port can be opened either fully or only partially depending on the need.

FIGS. 15-17 show various possible configurations of the ports, although additional embodiments would be conceived of that fit the nature of the claims. In an exemplary embodiment, the enclosure 1 may include large ports 10b as shown in FIG. 15, small ports 10c as shown in FIGS. 16 and 17, or both large ports 10b and small ports 10c as shown in FIGS. 16 and 17. Small ports 10c are configured such that small items may be passed in or out of the enclosure without significant relative loss of enclosure volume or pressure, regardless of frame availability, because the Environmental Control System (e.g. a fan) can increase the gas inflow to match the outflow. Large ports 10b permit the moving of large items like the instrument tray, neonates, et cetera in and out of the enclosure. FIG. 18 shows an exemplary embodiment of the port, in which a connector 29 splits a port in half, allowing it to act as a small port or large port. This bimodal port 10d ensures that any user can have access to both a small port and a large port. In addition to episodic access for large items, the ports can also provide ongoing access for lines, tubes, wires, and drains requiring access to external resources. The connector 29 may be a zipper slider that slides over the zipper teeth rows thereby adjusting the size of the port. Alternatively, it can be a material such as hook and loop fastener or magnets which provide rapidly reversible attachment. There are a number of ways the materials ports can be implemented. They must be easy to open and close repeatedly, such as can be achieved through the use of magnetic strips, hook-and-loop fasteners, plastic zippers, flexible inflatable tubes compressed against one another, or other methods.

D. Environmental Control System

Figure 11:
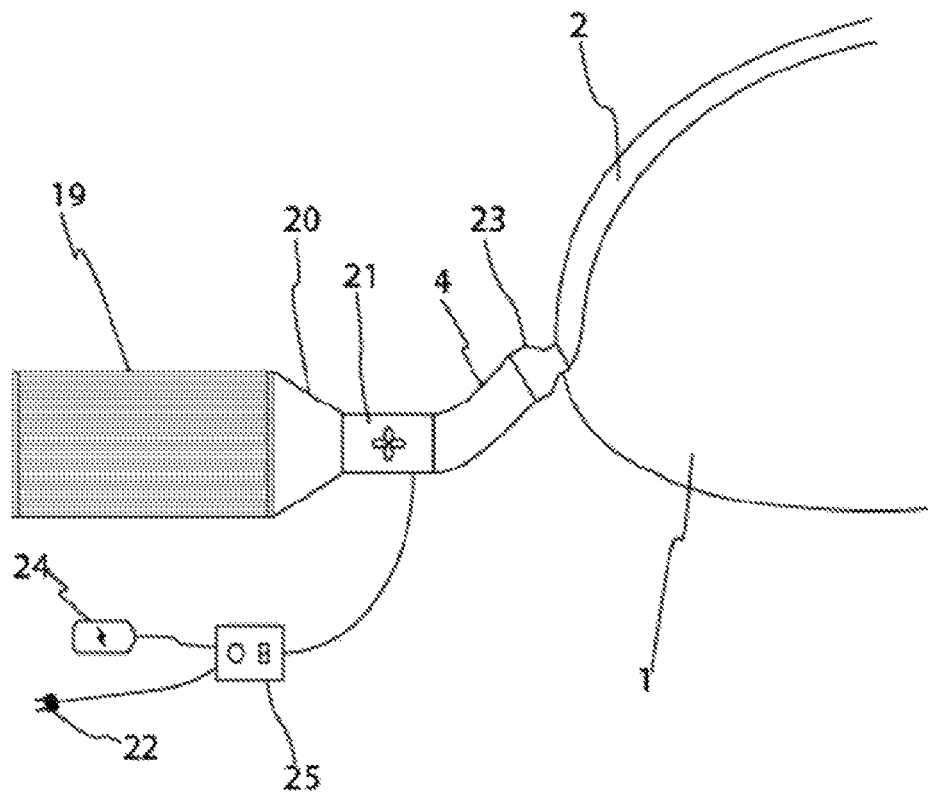
FIG. 11 is a schematic of the portions of the air supply system external to the enclosure.

The portable surgical system includes an environmental control system. In a preferred embodiment, as the one shown in FIG. 11, the environmental control system may include a HEPA filter 19, fan (blower with motor) 21, filter-blower adapter 20, battery 24, and control section 25, connected to the enclosure via sterile flexible tubing 23. These external components (i.e. components 19, 20, 21, 23, 24, and 25) are collectively referred to as air supply system. The battery 24 may be disposable or rechargeable, and the system can also run off the electrical grid 22 if the procedure occurs in a setting in which this is possible. The air supply system may be connected to the flexible overhead tube 2 of the surgical enclosure with flexible tubing so that the inlet height of the overhead airflow tube 2 can adjust based on the level of inflation of the enclosure 1. The HEPA filter immediately downstream of air inflow may be changeable and customizable such that it provides one or more other controls based on procedural need, such as humidity modulator filter, gas content with supply of medical gases, or temperature modulator with heat/cold sinks.

Figure 12:
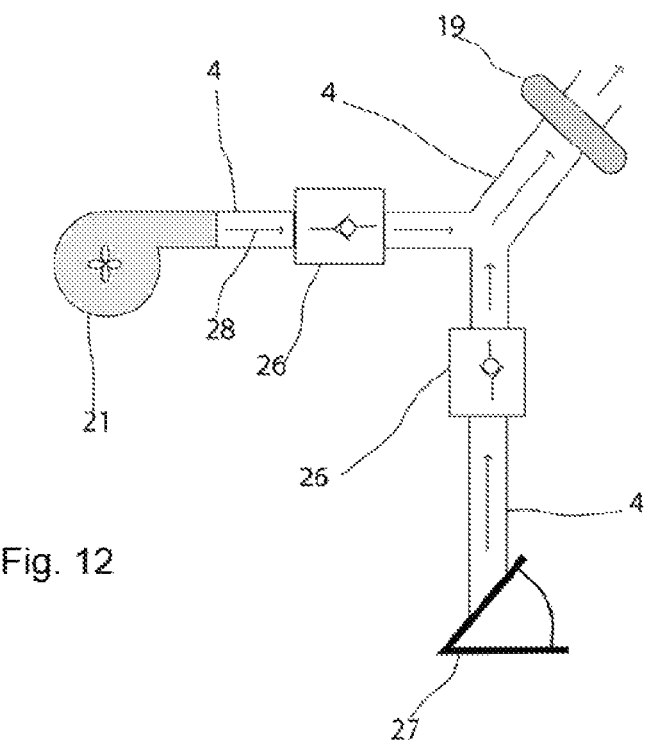
FIG. 12 is an alternate embodiment for the air supply system which incorporates a back-up manual pump.

In an alternative exemplary embodiment, the air supply system includes both an electrical fan 21 as well as a manual pump 27 as illustrated in FIG. 12. The manual pump 27 provides redundancy and may be used in the event of unavailability of electrical power supply or to provide higher flows without expending electrical power. The manual pump can be implemented in any number of mechanical setups familiar to practitioners in the art, including but not limited to via manual or pedal bellows-style pump or other general positive displacement pump, or manual or pedal rotary pump. The air supply system may further include one or more one-way valves 26 which allow the air from either only the electrical fan 21 or only the manual pump 27 to flow toward the plastic enclosure. The filter 19 is downstream of both electrical and manual air supply.

The external air supply system connects to the enclosure. In an exemplary embodiment, the air is supplied through an inlet and thereby blows through the entire enclosure cranially to caudally. Airflow adequacy may be checked by timing of inflation of the surgical enclosure 1 or by the rising of a windsock in the enclosure embodiment shown in FIG. 9. The windsock may include a short tube of flexible plastic of the same material as the enclosure side. In another exemplary embodiment, the inlet is connected to a horizontal manifold running side to side over the patient. The manifold may include an additional fold of the enclosure side plastic which is sealed together into tubular structure and perforated 3 to create parallel, uniform streams of laminar air outflow into the enclosure.

In a preferred exemplary embodiment the inlet is connected to a flexible tube, such as the overhead flexible tube 2 shown in FIGS. 1 and 2. The flexible tube 2 may include a plurality of perforations 3 acting as manifold. The flexible tube may run side to side or along the enclosure. The flexible tube may be formed by sealing a fold of the enclosure into a tubular structure. The flexible tube may be a collapsible tube that opens when air is blown into the enclosure and closes when air moves out of the enclosure such that transmural pressure from the enclosure favors tube collapse.

In a preferred exemplary embodiment, the flexible tube 2 may include a plurality of perforations 3 disposed such as to create parallel, uniform streams of laminar air outflow into the enclosure. Uniform airflow is accomplished in our preferred embodiment, as described by the design and manufacturing implementations detailed in FIGS. 20-22, by varying the density of perforations in the collapsible tube in which the density of perforations is higher at the end of the tube closer to the supply of the air 31 and the density of perforations decreases as the distance from the supply increases until the density is at its lowest value at 37.

Figure 20:
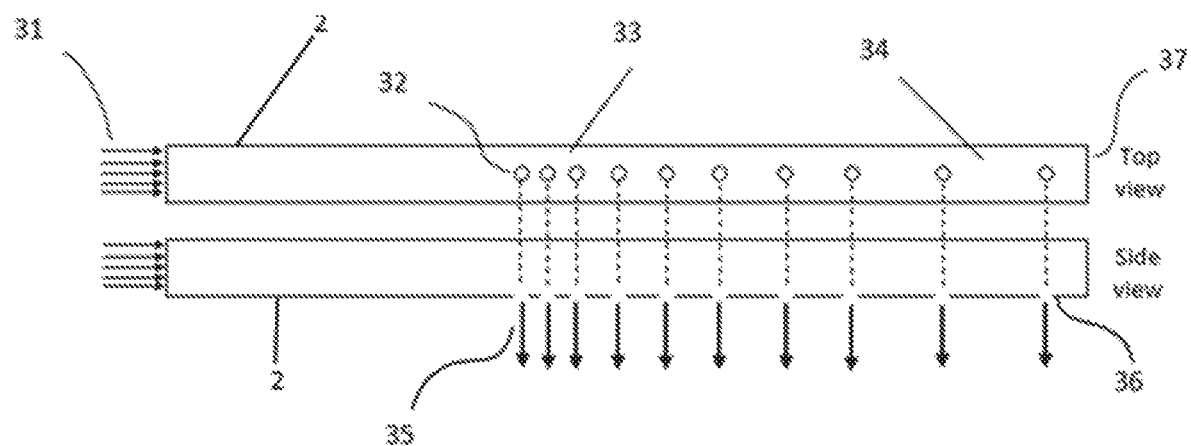
FIG. 20 is a schematic view of the airflow within the enclosure as traveling through the valve system continuously into and through the manifold system, with perforations varying in density along the manifold to produce uniform flow.

Inventors in this application came to the realization that nearly uniform air flow may be accomplished when the perforation density along the tube decreases according to the inverse of an elliptically shaped function. Starting from the observation that the pressure within an inviscid flow will rise along a streamline if the velocity of the airflow decreases, inventors of this application have found that in a perforated tube of constant cross sectional area, the velocity within a tube will drop as it passes perforations from which flow is emanating, as long as the flow is of nearly constant density which will be the case for flows of air substantially below the speed of sound. Further, inventors have come to the realization that the pressure in a perforated tube rises as the distance from the source increases and, as a result, the rate of flow from each perforation rises with distance from the source assuming the perforations are of constant cross sectional area. As shown in FIG. 20, the velocity is low 35 at locations close to the source 31 and the velocity is high 36 at locations far from the source 31. If the density of perforations were uniform, the flow of air would be too large at locations far from the source and too small at locations nearer to the source.

An exemplary embodiment of the invention discloses a flexible tube 2 (as shown by FIGS. 1, 2, 11, and 20) including a plurality of perforations disposed at such positions ($x_1$, $x_2$, $x_3$, $x_4$, ... $x_k$) along the tube as to create uniform air flow. The exemplary embodiment in FIG. 20 illustrates a tube including a plurality of perforations disposed in a single axial row along the tube. The tube may include multiple axial rows of perforations disposed on the circumference of the tubes such as to cover the entire surface of the tube or only a certain desired region, such as the region facing towards the surgical site. The multiple axial rows may be essentially parallel with each other and with the axis of the tube.

The perforations are disposed along the flexible tube such that the axial positions of the perforations along the flexible tube may follow a mathematical relation ($x_1$, $x_2$, $x_3$, $x_4$, ... $x_k$)=$\Phi$(V, d, D, $\rho$, k, L), where V is the air velocity from the source, D is the diameter of the tube, d is the diameter of the perforations, and $\rho$ is an air density, L is the length of the perforated section, and k the number of perforations in a row. The mathematical relation $\Phi$(V, d, D, $\rho$, k, L) is determined as explained hereinafter.

The positions of the perforations along the flexible tube may be expressed by a plurality of mathematical expressions: $x_1=\Phi_1$(V, d, D, $\rho$, k, L); $x_2=\Phi$(V, d, D, $\rho$, k, L); $x_3=\Phi_3$(V, d, D, $\rho$, k, L); ... $x_k=\Phi_k$(V, d, D, $\rho$, k, L); where V is the air velocity from the source, D is the diameter of the tube, d is the diameter of the perforations, and $\rho$ is an air density. The mathematical expressions $\Phi_1$(V, d, D, $\rho$, k, L), $\Phi_2$(V, d, D, $\rho$, k, L) ... $\Phi_k$(V, d, D, $\rho$, k, L) are determined as explained hereinafter and may be closed form expressions of (V, d, D, $\rho$, k, L).

The specific form of the perforation density needed for uniform air flow can be determined by an iterative computation.

Figure 21:
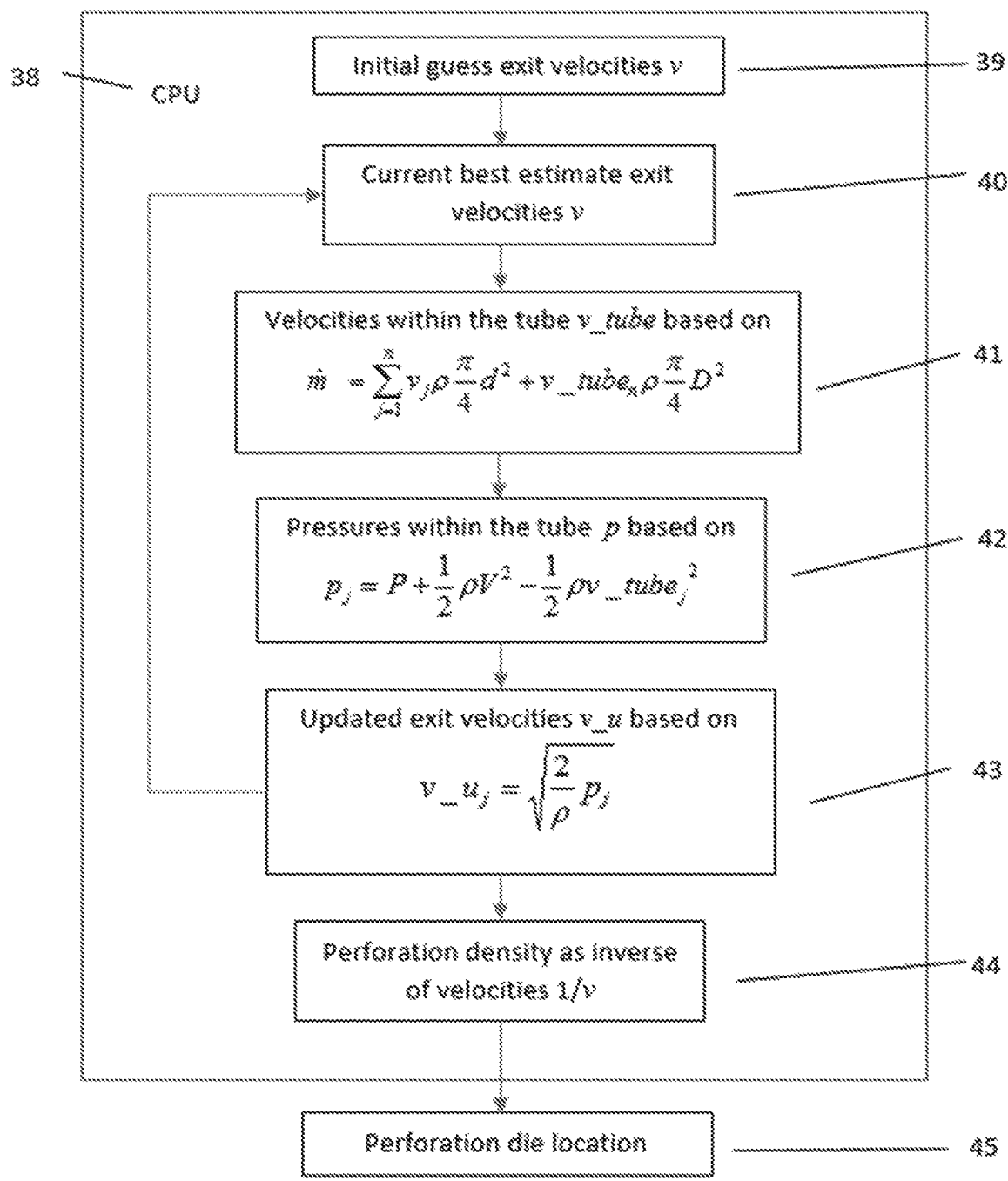
FIG. 21 is a schematic of a manufacturing process to produce the embodiment of FIG. 20.

The iterative computation may include a plurality of iterations, wherein each iteration includes a plurality of steps as described in FIG. 21. Within a CPU 38, begin with an assumed form of the exit velocities 39 such as a linearly increasing distribution. These assumed exit velocities will be denoted as $v_j$ with a unique subscript for each of the many holes numbered j=1 to k (i.e. velocities $v_1$, $v_2$, $v_3$, ... $v_k$ shown in FIG. 20 corresponding to perforations 1, 2, 3 ... k).

In a first step of the first iteration (see 40 in FIG. 21) it is assumed a form of the exit velocities 39. The assumed exit velocities (i.e. $v_1$, $v_2$, $v_3$ ... $v_k$) may be estimated as a linearly increasing distribution such as $$v_j = V \cdot \left(\frac{D^2}{k \cdot d^2}\right) \cdot (j-1),$$

where V is the axial air velocity at the source, D is the diameter of the tube, d is the diameter of the perforations, k is the number of perforations, and j is the index of the perforation or hole.

In a second step of the first iteration (see 41 in FIG. 21) the exit velocities ($v_1$, $v_2$, $v_3$, ... $v_k$) estimated at 40 are used to compute an estimate of the velocities within the tube v_tube 41 (i.e. v_tube$_1$; v_tube$_2$; v_tube$_3$; ...; v_tube$_k$). The velocity v_tube$_n$ is the axial velocity inside the portion of the tube between perforation "n" and perforation "n+1". Mass conservation requires that for any hole number n in a tube of diameter D with perforations of diameter d the following Equations are satisfied:

$$\dot{m} = \sum_{j=1}^{n} v_j \rho \frac{\pi}{4} d^2 + \text{v\_tube}_n \rho \frac{\pi}{4} D^2$$

-continued $$\dot{m} = V\rho\frac{\pi}{4}D^2$$

Where ρ is the air density, d is the diameter of the perforations, D is the diameter of the tube. The equations above provide the velocities inside tube (i.e. v_tube$_1$; v_tube$_2$; v_tube$_3$; . . . ; v_tube$_k$).

In a third step of the first iteration (see 42 in FIG. 21) the velocities inside the tube are used to calculate a set of pressures (p$_1$, p$_2$, p$_3$ . . . p$_k$) corresponding to each of the perforations as explained hereinafter. The flow axially within the interior of the tube may be modelled as inviscid flow. Bernoulli's equation may be used to provide a prediction of the pressure within the tube as a function of the velocities inside tube computed in the previous step (i.e. v_tube$_1$; v_tube$_2$; v_tube$_3$; . . . ; v_tube$_k$). It is assumed that the velocity in the tube near the end cap is zero and the velocity at the source is V and the constant air density is ρ. The pressure at the end of the tube farthest from the source is calculated as:

$$P = \frac{1}{2}\rho V^2$$

Then this value of the pressure P is used to estimate the pressures within the tube 42 at each of the many holes numbered j=1 to k as follows:

$$p_j P + \frac{1}{2}\rho V^2 - \frac{1}{2}\rho v\_tube_j^2$$

These pressures at each hole are computed and stored in a vector (p$_1$, p$_2$, p$_3$ . . . p$_k$).

In a fourth step of the first iteration (see 43 in FIG. 21), the pressures (p$_1$, p$_2$, p$_3$ . . . p$_k$) are used to calculate a new estimate of the exit velocities. The flow from the interior of the tube to the exit hole may be modelled as inviscid flow. Bernoulli's equation may be used to provide a prediction of the exit velocity as follows:

$$v\_u_j = \sqrt{\frac{2}{\rho}p_j}$$

One may use the relationship above k times (for each hole number from 1 to k) to calculate exit velocity estimates at each perforation or hole (i.e. v_u$_1$, v_u$_2$, v_u$_3$ . . . v_u$_k$). The updated exit velocity estimates v_u$_j$ are different from the initially assumed distribution (i.e. v$_1$, v$_2$, v$_3$, . . . v$_k$).

By mass conservation, the sum of the exit velocities must obey the relationship $$\dot{m} = \sum_{j=1}^{k} v_j \rho \frac{\pi}{4} d^2$$

In a fifth step of the first iteration the exit velocity estimates calculated in the fourth step are used to calculate a set of velocities (v$_{2-1}$, v$_{2-2}$, v$_{2-3}$, v$_{2-4}$, . . . v$_{2-k}$) to be used as starting point for a second iteration. The set of velocities are calculated as follows:

$$v_{2-j} = v_j \cdot \frac{(V\rho\pi D^2/4)}{\sum_{j=1}^{k}(v_j \rho \pi d^2/4)}$$

The set of velocities v$_{2-j}$ preserve the proportions among the calculated exit velocities v_u$_j$ but their magnitudes are adjusted to satisfy mass conservation by scaling each value. The scaling is performed by dividing each exit velocities by the sum $$\sum_{j=1}^{k}(v_j \rho \pi d^2/4)$$

and multiplying it by the known mass flow supply which is (Vρπ D$^2$/4).

The resulting exit velocity distribution (v$_{2-1}$, v$_{2-2}$, v$_{2-3}$, v$_{2-4}$, . . . v$_{2-k}$) is used as an updated estimate for a second iteration. The second through fifth steps (41 through 43 in FIG. 21) are repeated for the second iteration thereby obtaining a velocity distribution to be used as updated estimate for the third iteration. The process is iterated until it converges to a stable distribution of exit velocities (i.e. v$_{F1}$, v$_{F2}$, v$_{F3}$, v$_{F4}$ . . . v$_{Fk}$). The obtained distribution of exit velocities may be approximately elliptical if the total area of perforations is not small compared to the cross sectional area of the tube.

The density of the perforations 44 is determined by making it proportional to the inverse of the exit velocities. In an exemplary embodiment the position coordinates of the k perforations along the tube is denoted as x$_1$, x$_2$, x$_3$, x$_4$ . . . x$_k$ where x$_k$ is the distance between perforation k and a reference point on the tube between the air source and the first perforation. The positions x$_j$ (with j between 1 and k) may be calculated from the set of equations:

$$(x_{j+1} - x_j) = \alpha \cdot \frac{1}{v_{Fj}}; \text{(where } 1 \le j \le k\text{)}$$

Where α is determined by setting the distance between the first and last perforation to the desired length: (x$_k$−x$_1$)=L.

The above equations enable the skilled artisans to derive the mathematical expressions x$_1$=Φ$_1$(V, d, D, ρ, k, L); x$_2$=Φ$_2$(V, d, D, ρ, k, L); x$_3$=Φ$_3$(V, d, D, ρ, k, L); . . . x$_K$=Φ$_K$(V, d, D, ρ, k, L), thereby providing the positions and density of the perforations as function of parameters (V, d, D, ρ, k, L). The functions Φ$_n$(V, d, D, ρ, k, L) may be expressed by closed form expressions.

Alternatively, the set of parameters may be associated the resulting positions, (V, d, D, ρ, k, L)→(x$_1$, x$_2$, x$_3$, x$_4$, . . . x$_k$), determined by the above algorithm thereby forming the function (x$_1$, x$_2$, x$_3$, x$_4$, . . . x$_k$)=Φ(V, d, D, ρ, k, L). The function Φ(V, d, D, ρ, k, L) may be expressed by a closed form expression.

The positions and density of the perforations computed in the CPU 38 is implemented by a cutting die 45 which is located at positions over the clear plastic tube according to the desired perforation positions/density (i.e. x$_1$, x$_2$, x$_3$, x$_4$, . . . x$_k$). The resulting perforations distribution will essentially follow an inverse of a elliptical function. By making the density of perforations an inverse of an elliptically shaped function, the resulting air distribution within the surgical area is uniform throughout providing an advantage in quality of the surgical outcome.

In an exemplary embodiment of the invention a method for manufacturing a portable surgical system may include: (1) running on a CPU the iterative computation described above; (2) receiving, from the CPU, at a machine for cutting perforations into the tube material a set of numbers corresponding to the positions ($x_1$, $x_2$, $x_3$, $x_4$, . . . $x_k$) of the perforations; (3) cutting the perforations into the tube materials at positions ($x_1$, $x_2$, $x_3$, $x_4$, . . . $x_k$) received from CPU.

Figure 22:
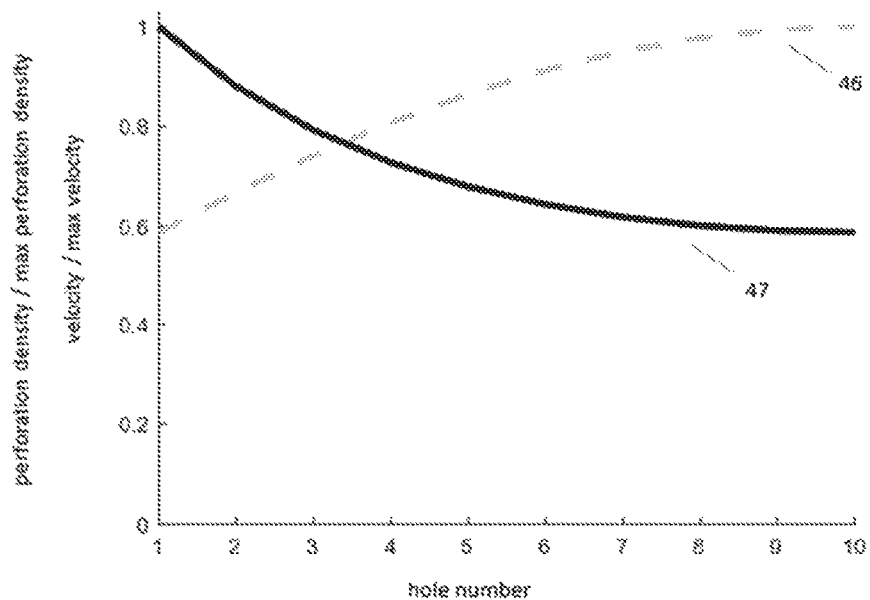
FIG. 22 is a graph relating manifold perforation density and air exit velocity from the embodiment of FIG. 20.

As an illustration, the resulting velocity distribution and perforation density distribution are graphically depicted in FIG. 22. This depiction is for a case with ten perforations in the collapsible flexible tube and it will be understood that the method generalizes to other numbers of perforations. The hole number is on the x axis and the exit velocity 46 and perforation densities 47 (normalized so that the maximum values are unity) are represented on the y axis.

Figure 23:
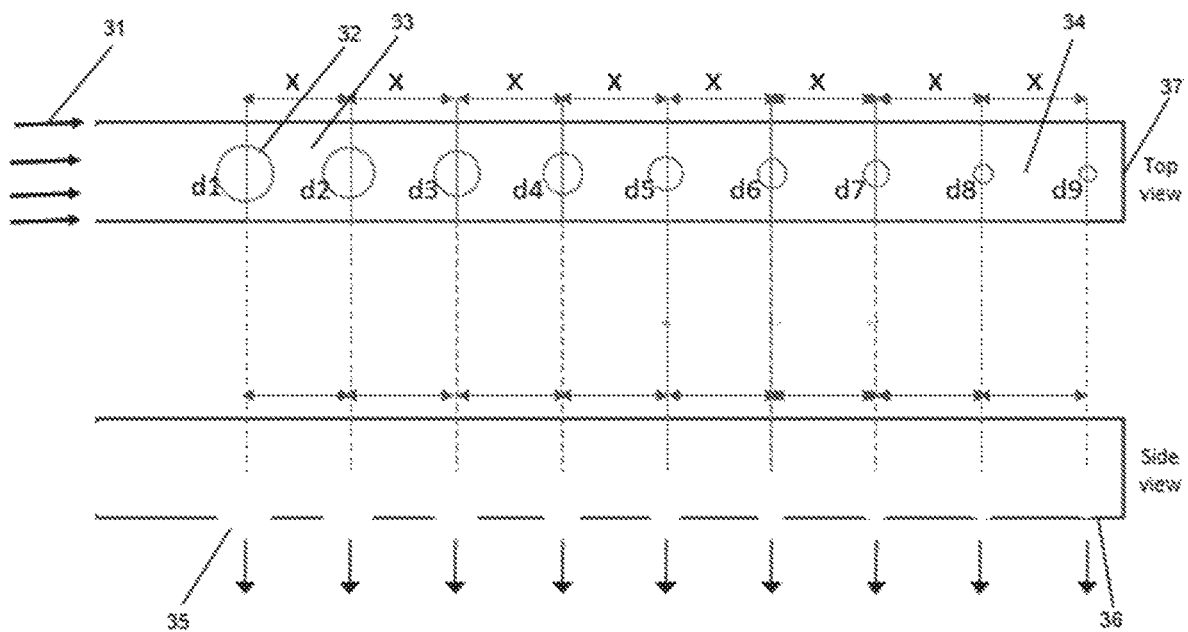
FIG. 23 is a schematic view of the airflow within the enclosure as traveling through the valve system continuously into and through the manifold system, with perforations varying in diameter along the manifold to produce uniform flow.

In another exemplary embodiment the above uniform air distribution can also be achieved via an alternative configuration of the perforations in the flexible tube as shown in FIG. 23. In this configuration the perforations are equidistant (distance depicted as x in FIG. 23) while the diameter of the perforations varies (i.e. $d_1$, $d_2$, $d_3$, . . . $d_k$) such that the air flow through each of the perforations is identical and 1/k proportion of the total flow through the manifold. The goal in such a case is to integrate the total area of perforation for each given, uniform distance $x_i$. A system of dies may be used to cut the correct perforation diameter at points $x_1$, $x_2$, $x_2$, . . . , $x_k$.

Another alternative embodiment of the air handling system inside the enclosure instead runs airflow longitudinally caudally to cranially, along center of top.

Figure 13:
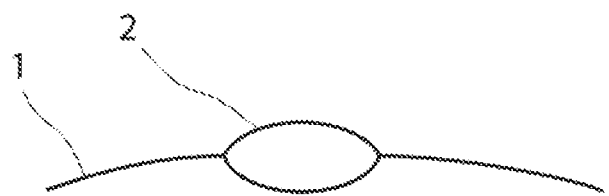
FIG. 13 shows the axial view with the overhead inlet tube valve in the enclosure open during active air inflow, signaling adequate flow.
Figure 14:
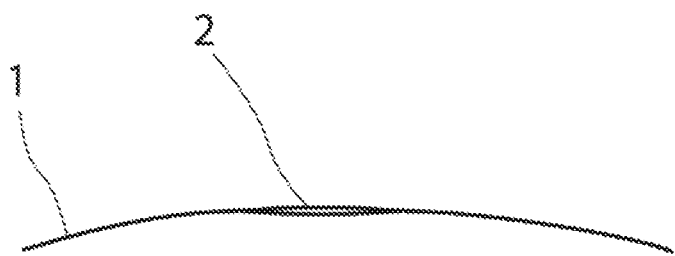
FIG. 14 shows the axial view with the tube valve FIG. 13 pinched closed by the enclosure's positive pressure, thus sealing the system and preventing backflow.

The portable surgical system may include a flexible tube 2 (as depicted in FIGS. 1, 2, 11, and 20) configured to act as a valve system, as described with respect to FIGS. 13 and 14, such as to prevent air backflow from the surgical enclosure into the fan and filter. FIGS. 13 and 14 show a cross-section through a portion of the surgical enclosure 1 and the flexible tube 2 attached to or incorporated into the surgical enclosure 1. FIG. 13 shows the flexible tube in an expanded state when air is blown from the air supply system 5 into the surgical enclosure. FIG. 13 shows the axial view with the overhead inlet tube valve in the enclosure open during active air inflow, signaling adequate flow. FIG. 14 shows the axial view with the tube valve FIG. 13 pinched closed by the enclosure's positive pressure, thus sealing the system and preventing backflow. FIG. 14 shows the flexible tube in a collapsed state when air pressure inside the enclosure is pushing the air from the enclosure towards outside the enclosure. The collapsed tube 2 prevents the air from exiting the enclosure.

The collapsible tube may be made of flexible material such as to switch from open to close state, and vice versa, based on airflow. The airflow passes from air supply system first through an inflow tube valve 2 comprising a sealed tube of collapsible plastic. When there is net positive airflow through the tube toward the manifold in this configuration, the transmural pressure is positive relative to the enclosure, and the tube is forced open. When there is no airflow or reversed airflow, the transmural pressure drops relative to the enclosure, causing longitudinal collapse of the tube. This tube valve reduces further flow in the setting of enclosure excess pressurization as the enclosure positive pressure produces transmural pressure favoring valve collapses; prevents flow reversal as enclosure positive pressure seals off air outflow through the valve; and also serves as an indicator of adequate airflow indicator by virtue of its inflation. The airflow then proceeds to a manifold 3, implemented as above in the horizontal manifold system. The relative lengths of the valve and manifold are determined by procedural needs for pressure and airflow; but the manifold should preferably extend at least the full length of the operating-section.

Figure 24:
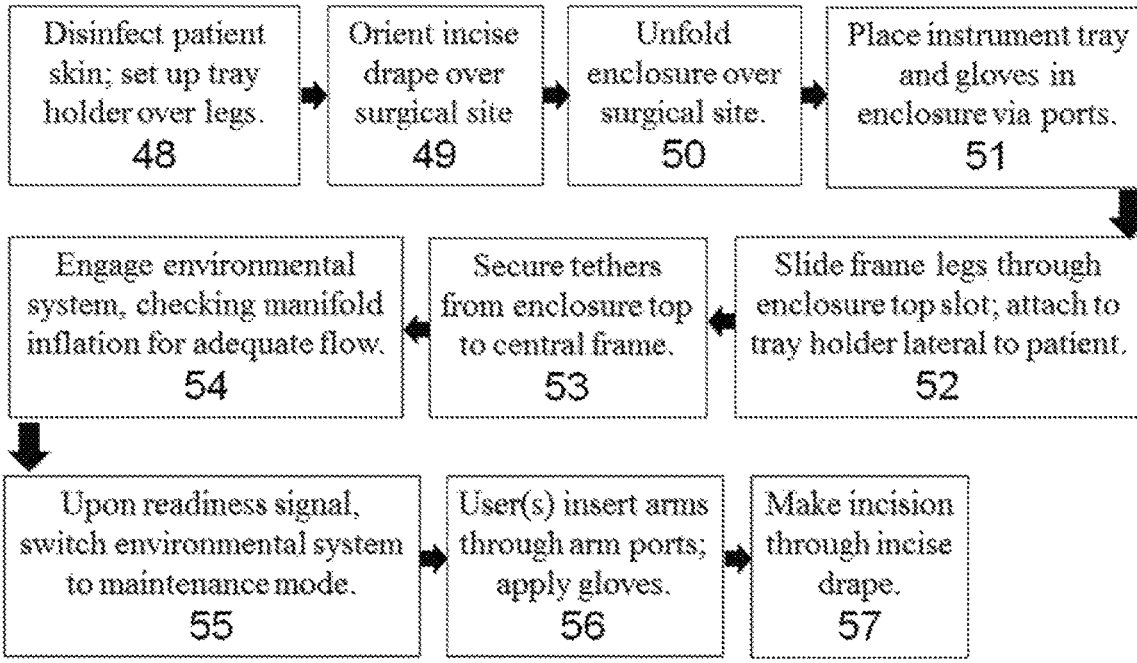
FIG. 24 is a schematic sample setup workflow for the frame embodiment described in FIGS. 3 and 4.

E. Method for Setup of Surgical Enclosure with Respect to Standard Surgical Workflow An exemplary embodiment of the present invention also discloses a method for using the ultraportable surgical system comprising the steps described in FIG. 24 flowchart. The sterile field, which corresponds to the draped areas in standard procedural setup, includes the entire enclosed area and the sleeves. This method applies for all embodiments utilizing the incise drape interface. The users first disinfect the skin 48 of the patient as per usual protocol using any of the standard skin antiseptic agents, provided they are permitted to dry fully before applying the incise drape. Users then orient 49 the enclosure with the incise drape over the planned surgical site and the instrument-section extending caudally, set up the enclosure 50, and add needed instrument tray and gloves via the material ports 51. As the entire system comes pre-sterilized in packaging, the air inside is sterile until the sterile instrument tray is placed. The enclosure is then connected to the frame 52 which in turn is stabilized on the instrument tray holder, strapped down for additional stabilization against the patient or operating table 53, and the environmental control system is turned on 54. Inlet tube valve inflation is utilized as the indicator of adequate airflow through the environmental system. The first inflation is thus also an initial purge of any contamination introduced during that step. When the system is adequately inflated, or an indicator is activated, the environmental system is switched to maintenance mode 55. At this point, users can place arms through the arm ports, apply gloves or overgloves in standard protocol 56, and initiate the procedure 57. Maintenance mode is an option for procedures in which the air changes are planned to be different than the ones used for initial inflation or that opts to recycle air through an exhaust system to prolong filter life span, but it can also be no change from prior mode. For arm port use, it is recommended that providers wear one pair of sterile undergloves, then don the second pair of gloves inside the enclosure in standard double gloving procedure to seal the sleeve port embodiments of the arm ports.

At the end of the procedure following any appropriate skin closure and dressing application, users remove the tray and any items from inside the enclosure, clear any blood or bodily fluids within the enclosure, doff gloves then remove arms from the arm ports, turn off the environmental control system, remove the air supply tubing from the air handling inlet, pull the enclosure off of the frame as well as off of the patient, and dispose of the enclosure.

Figure 25:
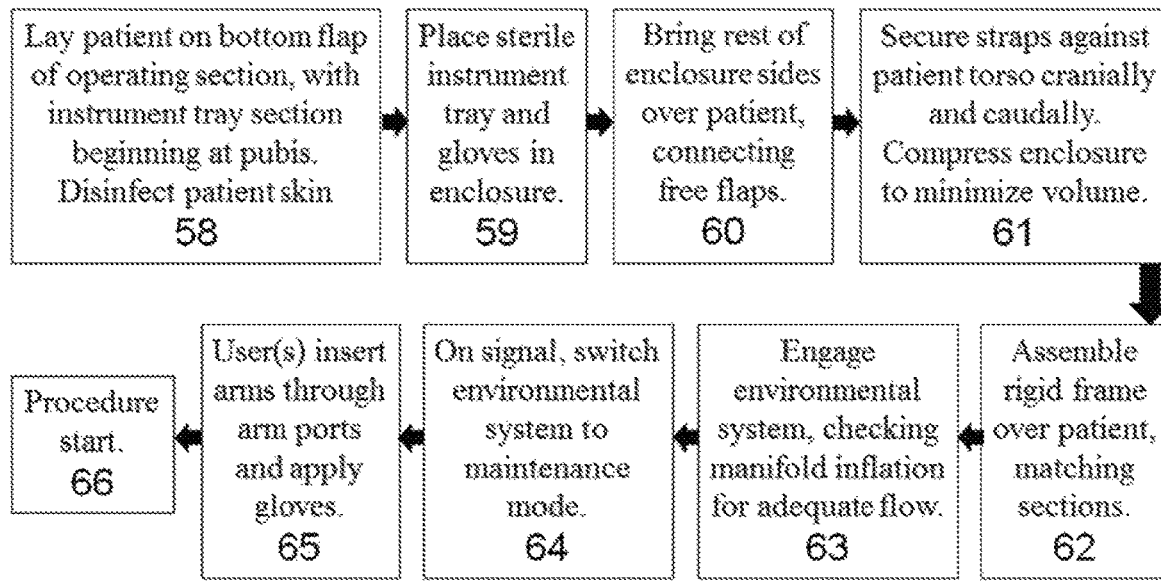
FIG. 25 is a schematic sample setup workflow for the frame embodiment described in FIG. 9.

For embodiment systems not utilizing incise drapes, setup methodology is described in FIG. 25. In this scenario, the user positions the patient directly over the bottom flap of the operating-section 58, places instrument and gloves in planned enclosure 60, connects the bottom flap against the side of the enclosure 60, clinch the enclosure cranially and caudally against the patient 61, then assembles the frame while connecting to the enclosure 62. The environmental control system is engaged 63 with monitoring of wind sock at air inflow to check for adequate flow. When the enclosure is adequately filled with clean air as shown by indicator (based on air changes), the environmental system is switched to maintenance mode 64. At this point, users can place arms through the arm ports, apply gloves or overgloves in standard protocol 65, and initiate the procedure 66.

Although only a few embodiments have been described in detail above, those skilled in the art can recognize that many variations from the described embodiments are possible without departing from the spirit of the invention.

F. Supporting Studies

Figure 26:
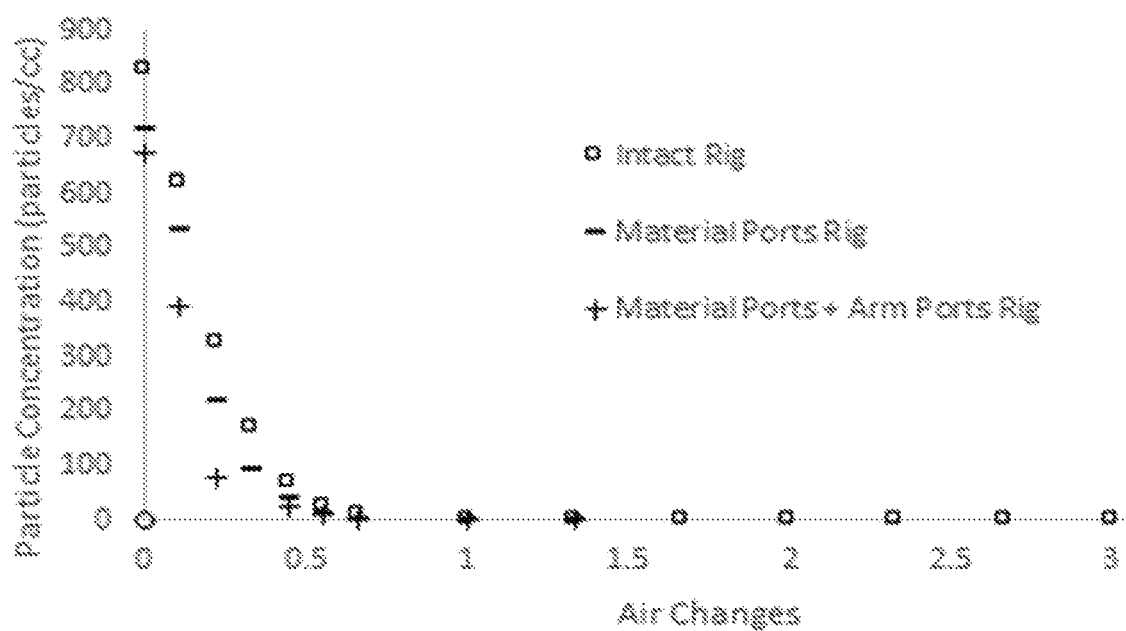
FIG. 26 shows a graph of the particle concentration inside the enclosure as function of environment parameters as obtained from tests on a prototype portable surgical system.

Inventors have implemented various embodiments, such as the ones described herein among others, by manufacturing and testing fully self-contained portable surgical systems. In Teodorescu et al (2016) inventors have demonstrated an early proof of concept showing that the enclosure, even in absence of environmental control system engagement, provided 100% protection against external active particulate contamination (FIG. 26). Inventors have further demonstrated that even with enclosure contamination to level found in machine shop utilizing charcoal burning. 2.25 air changes were adequate to consistently bring contaminant particulate levels to 0 particles per cubic centimeter. Subsequent systems reduced susceptibility to enclosure contamination and improved setup speeds through the protocols described above (e.g. as described in Teodorescu et al 2017).

The features of the invention disclosed herein, as specified by actual surgical end-users, distinguish it from prior art by enhancing usability, ergonomics, independence from external resources, and reliability under field conditions. The inclusion within the enclosure of only the surgical site, excluding the remainder of the patient body from the sterile field, particularly high-contaminant regions such as the oropharynx or the genitals, improves the efficacy of the system. The invention's ability to isolate the surgical wound's contaminant production, such as blood and bodily fluids, and contain these through the life cycle of the product, is also a key feature.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalent.

G. References

The following documents cited herein do not represented admitted prior art. The following documents cited herein are hereby incorporated by reference: [1] WO/2014/145032. (GNANASHANMUGAM), 15 Mar. 2013; [2] WO2011041665 A2, (HENDERSON), 1 Oct. 2009; [3] WO2005092229, (KRIEK), 24 Mar. 2004; [4] US20070102005 A1. (BONUTTI), 28 Aug. 2001; [5] U.S. Pat. No. 6,199,551 B1, (KUSLICH), 8 Dec. 1998; [6] U.S. Pat. No. 5,299,582 A. (POTTS), 16 Sep. 1991; [7] WO8606272, (SCOTT), 23 Apr. 1985; [8] U.S. Pat. No. 4,367,728 A. (MUTKE), 7 Sep. 1979; [9] U.S. Pat. No. 4,275,719 A. (MAYER), 30 Mar. 1979; [10] U.S. Pat. No. 3,051,164 A. (TREXLER), 17 Aug. 1959; [11] American Society of Heating. Refrigeration and Air-Conditioning Engineers (2011). Health Care Facilities (I-P). In ASHRAE 2011 Handbook-HVAC Application. Atlanta: ASHRAE; [12] Allegranzi, B., Bagheri Nejad. S., Combescure, C., Graafmans, W., Attar, H., Donaldson, L., and Pittet, D. (2011). Burden of endemic health-care-associated infection in developing countries: a systematic review and meta-analysis. Lancet. 377 (9761): 228-41; [13] Edmiston, C. E., Seabrook, G. R., Cambria, R. A., et al. (2005). Molecular epidemiology of microbial contamination in the operating room environment: is there a risk for infection. Surgery. 138 (4): 573-582. [14] Sehulster, L. and Chinn, R. Y. W., 2003, "Guidelines for Environmental Infection Control in Health-Care," www.cdc.gov/mmwr/preview/mmwrhtml/rr5210a1.htm. [15] Selcen Kilinc, F. (2015). A review of isolation gowns in healthcare: fabric and gown properties. J Eng Fiber Fabr. 10 (3): 180-190; [16] Teodorescu D L, Miller S A, Jonnalagedda S. SurgiBox: An ultraportable system to improve surgical safety for patients and providers in austere settings. IEEE Xplore GHTC 2017 (accepted, pending publication); [17] Teodorescu D L, Nagle D, Hickman M, King D R. An ultraportable device platform for aseptic surgery in field settings. ASME J Medical Devices. J. Med. Devices 10(2), 020924 (May 12, 2016); [18] Whyte, W., Hodgson, R., and Tinkler, J. (1982). The importance of airborne bacterial contamination of wounds. Journal of Hospital Infection. 3:123-135.

The invention claimed is:

1. A portable surgical system comprising:
  a flexible enclosure separating a surgical environment inside the flexible enclosure from a user environment outside the flexible enclosure, the flexible enclosure comprising:
    a drape configured to be disposed on a body of a patient to enclose a surgical site of the body of the patient, the drape comprising a releasable adhesive to engage with a skin of the patient;
    one or more areas of high optical clarity for viewing an inside of the flexible enclosure;
    a flexible tube attached to the inside of the flexible enclosure and in use extends longitudinally caudally to cranially along the body of the patient, the flexible tube being connected to an environmental control system and being disposed, in part, above the surgical site; and
    a plurality of perforations disposed along an axial direction of the flexible tube according to determined diameters and positions to support an essentially uniform laminar airflow in the flexible tube such that air flow through each of the perforations is identical, wherein the perforations have equal diameters and a positional distribution of non-uniform density; and
  the environmental control system configured to supply air to the flexible tube of the flexible enclosure and to create essentially sterile conditions inside the flexible enclosure; and
  one or more ports for accessing the surgical site.

2. The portable surgical system of claim 1, wherein:
  the flexible enclosure further comprises at least one instrument section configured to accommodate inside the flexible enclosure an instrument tray.

3. The portable surgical system of claim 2, wherein the instrument tray is disposed proximately to the surgical site above a portion of the body of the patient.

4. The portable surgical system of claim 1, wherein:
  the system further comprises a frame configured to support the flexible enclosure, wherein the frame is disposed outside the flexible enclosure.

5. The portable surgical system of claim 1, further comprising one or more arm ports disposed into sides of the flexible enclosure, wherein each arm port is configured such that the arm port permits an arm of a user to access the surgical site without substantially allowing either inward contamination of the surgical site by external air or outward contamination of a provider by contaminants emanating from the body of the patient; and
   wherein at least some of the arm ports are configured to enable an operating instrument to access the surgical site.

6. The portable surgical system of claim 1, further comprising one or more material ports disposed into sides of the flexible enclosure, wherein the material ports are configured so as to permit materials to be taken into and out of the flexible enclosure without substantially allowing either inward contamination of the surgical site by external air or outward contamination of a provider by contaminants emanating from the body of the patient.

7. The portable surgical system of claim 1, wherein the flexible tube comprises in whole or in part a collapsible tube configured to assume an open state while airflow through the collapsible tube exerts radial outward pressure sufficient to overcome a radial inward pressure of the flexible enclosure, and to assume a collapsed closed state when the airflow through the collapsible tube is low such that the pressure exerted by the airflow is less than the radial inward pressure of the flexible enclosure; and
   wherein the open or closed state of the collapsible tube serves as an indicator of airflow status to the flexible enclosure.

8. The portable surgical system of claim 1, wherein:
the releasable adhesive comprises antimicrobial impregnation.

9. The portable surgical system of claim 1, wherein the positional distribution of the perforations along the flexible tube essentially follow an inverse of an elliptically shaped function.

10. The portable surgical system of claim 1, wherein the positions of the perforations along the flexible tube are determined according to a specific set of mathematical expressions.

11. The portable surgical system of claim 1, wherein the positions of the perforations along the flexible tube are determined by a computation comprising a plurality of iterations, the iterations further comprising:
   a first step wherein a set of exit flow velocities is assigned to each of the perforations;
   a second step wherein the set of exit velocities assigned in the first step is used to calculate a set of longitudinal flow velocities in the flexible tube;
   a third step wherein the set of longitudinal flow velocities calculated in the second step are used to calculate a set of pressures corresponding to each of the perforations;
   a fourth step wherein Bernoulli's equation and the set of pressures calculated in the third step are used to calculate an updated set of exit velocities corresponding to each of the perforations; and
   a fifth step wherein the updated set of exit velocities determined in the fourth step are scaled such as to satisfy mass conservation, thereby obtaining a set of estimated velocities corresponding to each of the perforations,
   wherein the set of estimated velocities determined in the fifth step of an iteration are used as input for a next iteration.

12. The portable surgical system of claim 11, wherein the set of exit flow velocities assigned to each of the perforations in the first step of a first iteration follow a linearly increasing distribution.

13. The portable surgical system of claim 11, wherein the computation comprises a number N of iterations, such that N sets of estimated exit velocities determined after running each of the N iterations converges to a stable distribution of exit velocities.

14. A portable surgical system comprising:
   a flexible enclosure separating a surgical environment inside the flexible enclosure from a user environment outside the flexible enclosure, the flexible enclosure comprising:
      a drape configured to be disposed on a body of a patient to enclose a surgical site of the body of the patient, the drape comprising a releasable adhesive to engage with a skin of the patient;
      one or more areas of high optical clarity for viewing an inside of the flexible enclosure;
      a flexible tube attached to the inside of the flexible enclosure and in use extends longitudinally caudally to cranially along the body of the patient, the flexible tube being connected to an environmental control system and being disposed, in part, above the surgical site; and
   a plurality of perforations disposed along an axial direction of the flexible tube according to determined diameters and positions to support an essentially uniform laminar airflow in the flexible tube such that air flow through each of the perforations is identical, wherein the positions of the perforations are determined as a function of a stable distribution of exit velocities according to:

$$(x_{j+1} - x_j) = \alpha \cdot \frac{1}{v_{Fj}}; \text{(where } 1 \leq j \leq k),$$

wherein $\alpha$ is determined by setting a distance between a first perforation and a last perforation to a length of $x_k - x_1$;
      wherein the perforations have equal diameters and a positional distribution of non-uniform density; and
   the environmental control system configured to supply air to the flexible tube of the flexible enclosure and to create essentially sterile conditions inside the flexible enclosure; and
   one or more ports for accessing the surgical site.

15. A portable surgical system comprising:
   a flexible enclosure separating a surgical environment inside the flexible enclosure from a user environment outside the flexible enclosure, the flexible enclosure comprising a flexible tube configured to receive air from an environmental control system,
   wherein the flexible tube:
      in use, extends longitudinally caudally to cranially along a body of a patient;
      comprises a plurality of perforations disposed along an axial direction of the flexible tube according to determined diameters and positions to support an essentially uniform laminar airflow in the flexible tube such that air flow through each of the perforations is identical; and
      is configured to operate as a valve system to prevent air backflow from the flexible enclosure;
   wherein the perforations have equal diameters and a positional distribution of non-uniform density;
   wherein the flexible tube is in a collapsed state when air pressure inside the flexible enclosure is pushing air from the flexible enclosure towards the user environment; and wherein the flexible tube is in an expanded state when air is flowing from the environmental control system into the surgical environment inside the flexible enclosure.

16. The portable surgical system of claim 15, wherein:

the flexible tube is in the expanded state when the air is received from an air supply system of the environmental control system; and the flexible tube is in the collapsed state when air pressure within the flexible enclosure is pushing air outwardly in a direction outside the enclosure.

17. The portable surgical system of claim 15, wherein:

the flexible tube is configured to operate in a plurality of states based on airflow, the plurality of states comprising an open state and a closed state;

in the open state, the flexible tube is configured to receive a net positive airflow from an air supply system of the environmental control system; and in the closed state, the flexible tube is configured to prevent flow reversal in response to no airflow or reverse airflow occurring from the air supply system to the flexible enclosure.

* * * * *

UNITED STATES PATENT AND TRADEMARK OFFICE
CERTIFICATE OF CORRECTION

| | | |
|---|---|---|
| PATENT NO. | : 12,201,486 B2 | Page 1 of 1 |
| APPLICATION NO. | : 16/317892 | |
| DATED | : January 21, 2025 | |
| INVENTOR(S) | : Debbie Lin Teodorescu et al. | |

It is certified that error appears in the above-identified patent and that said Letters Patent is hereby corrected as shown below:

In the Specification

Column 1, Line 14 (Approx.), delete "Environments."" and insert -- Environments," --.

In the Claims

Column 18, Line 35, In Claim 14, delete "a" and insert -- α --.

Signed and Sealed this
Eighteenth Day of March, 2025

Coke Morgan Stewart
*Acting Director of the United States Patent and Trademark Office*